United States Patent [19]
Fowler

[11] Patent Number: 5,987,652
[45] Date of Patent: Nov. 23, 1999

[54] RELEASABLE STRAPPING SYSTEM FOR PROTECTIVE EYEWEAR

[76] Inventor: Raymond Allen Fowler, P.O. Box 545, Rte. 175, Campton, N.H. 03223

[21] Appl. No.: 09/049,795

[22] Filed: Mar. 27, 1998

[51] Int. Cl.[6] ........................................ A42B 3/18
[52] U.S. Cl. ...................................... 2/424; 2/452
[58] Field of Search ............... 2/424, 426, 452, 2/5, 10, 6.3, 6.7; 351/155, 157; 128/201.24

[56] References Cited

U.S. PATENT DOCUMENTS

| | | | |
|---|---|---|---|
| 4,686,712 | 8/1987 | Spiva | 2/10 |
| 4,713,844 | 12/1987 | Westgate | 2/424 X |
| 4,796,308 | 1/1989 | Bourgeois | 2/10 |
| 4,918,753 | 4/1990 | Mermillod | 2/10 |
| 5,291,880 | 3/1994 | Almovist et al. | 2/5 X |
| 5,303,428 | 4/1994 | Pernicka | 2/428 |
| 5,732,415 | 3/1998 | Boyd | 2/426 |

*Primary Examiner*—Peter Nerbun
*Attorney, Agent, or Firm*—Davis and Bujold

[57] ABSTRACT

A protective eyewear housing supporting a transparent lens. A first end of the housing has a first strap attached thereto and a second opposite end of the first strap has a first clip member attached thereto. A second opposed end of the housing has a first end of a second strap affixed thereto and a second opposite end of the second strap has a second clip member attached thereto. The helmet supports a pair of spaced apart clip housings, and the clip housings are sized to matingly engage with one of the first and second clip members for releasably securing the protective eyewear to the helmet.

20 Claims, 4 Drawing Sheets

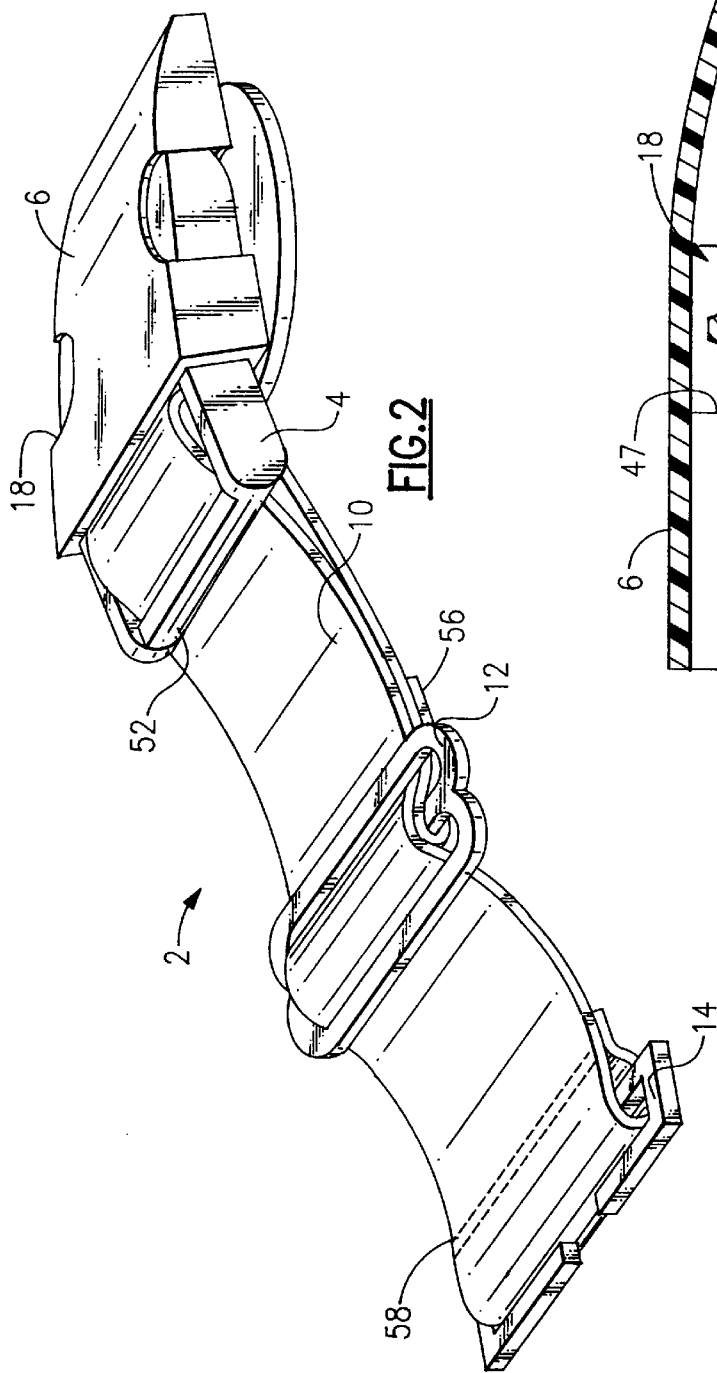
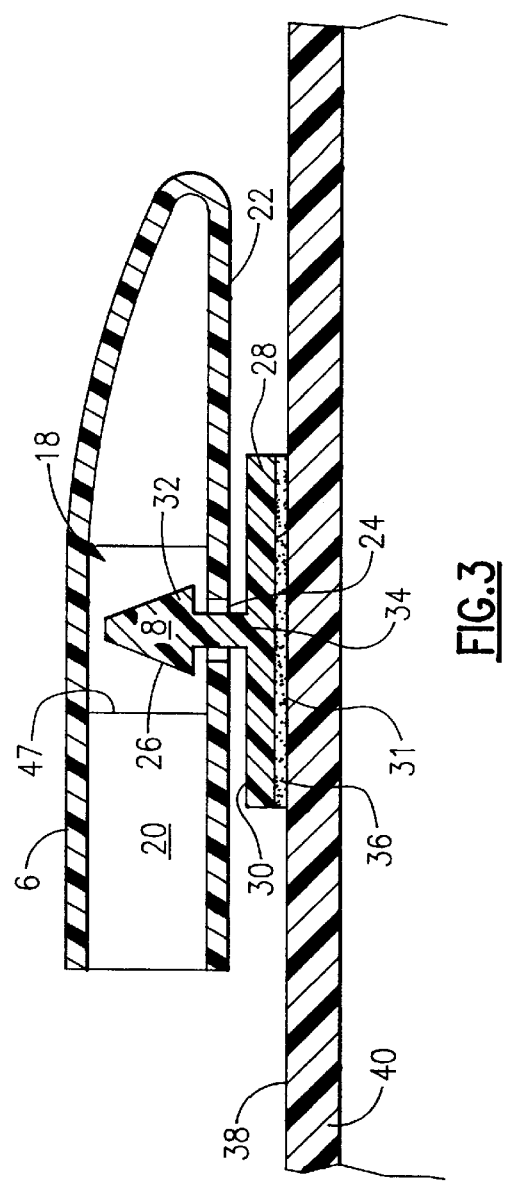

RELEASABLE STRAPPING SYSTEM FOR PROTECTIVE EYEWEAR

FIELD OF THE INVENTION

This invention relates to a releasable strap arrangement for releasably securing protective eyewear, such as goggles, glasses, sun glasses, a wind screen, etc., to a helmet, such as a motorcycle, ski or bicycling helmet.

BACKGROUND OF THE INVENTION

In the prior art, a rear central portion of the helmet is typically provided with a releasable flexible latch mechanism for securing an intermediate portion of an elongate continuous strap to the helmet to prevent the strap from sliding either upwardly or downwardly along the exterior surface of the helmet. Opposed ends of the elongate continuous strap, in turn, are attached to a pair of goggles, glasses, sun glasses, or a wind screen, etc. One drawback with this arrangement is that when the goggles, for example, are to be removed for cleaning or to wipe the user's face, it is difficult to disconnect the latch mechanism of the helmet. Consequently, the user is typically required to completely remove the helmet from his/her head in order to clean the goggles, or to wipe the user's face, and such procedure is generally inconvenient to the user and is to be avoided.

SUMMARY OF THE INVENTION

Wherefore, it is an object of the present invention to overcome the aforementioned problems and drawbacks associated with the prior art designs.

In particular, the present invention seeks to provide a quick and easy way to attach protective eyewear, such as a pair of goggles, glasses, sun glasses, or a wind screen, etc., to a helmet or the like, as well as facilitating quick and easy removal therefrom without having to remove the helmet from the user's head.

The invention relates to a protective eyewear system for protecting eyes of a user, the protective eyewear system comprising a protective eyewear housing supporting a transparent lens; a first end of the protective eyewear housing having a first end of a strap attached thereto, and a second opposite end of the first strap having a first clip member attached thereto; and a second opposed end of the protective eyewear housing having a first end of a second strap affixed thereto, and a second opposite end of the second strap having a second clip member attached thereto; in combination with a helmet, wherein the helmet supports a pair of spaced apart clip housings, and the clip housings are each sized to matingly engage with one of the first and second clip members for securing the protective eyewear to the helmet.

BRIEF DESCRIPTION OF THE DRAWINGS

The invention will now be described, by way of example, with reference to the accompanying drawings in which:

FIG. 2 is a diagrammatic view showing the assembled strap member arrangement for one strap member according to the present invention;

FIG. 3 is a diagrammatic cross-sectional view of the helmet, the attachment member and the clip housing;

DESCRIPTION OF THE PREFERRED EMBODIMENTS

Figure 1:
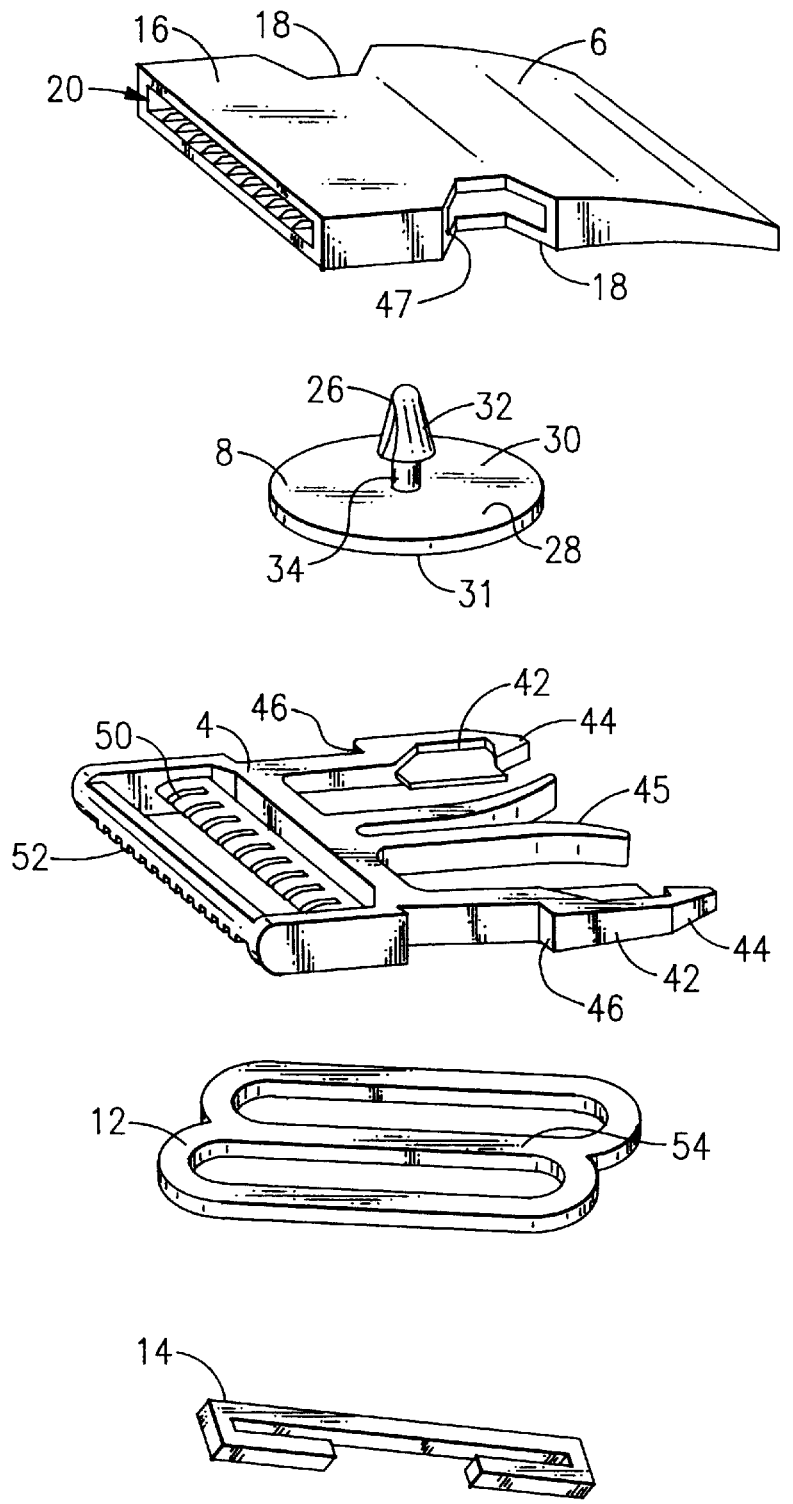
FIG. 1 is an exploded view of the components to form and secure each strap member for the protective eyewear according to the present invention.

Turning now to FIGS. 1–4, a detailed description concerning the present invention will now be provided. As can be seen in those Figures, the present invention generally comprises a strap member 2, a female clip housing 6 and an attachment member 8. The strap member 2 comprises an elongate strap 10 interconnecting a male clip member 4 with a coupling member 14; and an adjustment member 12 is engaged with an intermediate section of the elongate strap 10 to facilitate length adjustment of the strap 10.

The clip housing 6 has an exterior surface 16 which is provided with a pair of opposed openings 18 in the side walls thereof. The exterior surface 16 defines a generally hollow cavity 20 which is sized to intimately receive a major portion of the leading end of the clip member 4 therein. A further detailed description concerning the same will follow. A bottom surface 22 of the housing is provided with a housing aperture 24 therein to facilitate receiving and locking engagement with a mushroom protrusion element 26 of the attachment member 8. A further detailed description concerning the function and interaction between these components will be provided below.

The attachment member has a base 28 with a first surface 30 and an opposed second surface 31. The first surface supports the centrally located mushroom protrusion element 26 which extends perpendicularly therefrom. The mushroom protrusion element 26 has a head 32 which is larger in diameter than the housing aperture 24 provided in the clip housing 6 (FIG. 3). The head 32 includes a sufficient taper, at a remote end thereof, to facilitate passage of the head 32 through the housing aperture 24. Once the head 32 passes completely through the housing aperture 24, the head 32 facilitates retention of the clip housing 6 to the attachment member 8. A stem 34 interconnects the head 32 with the base 28, and the stem 34 is slightly smaller in size than the housing aperture 24 to facilitate rotation of the clip housing 6 relative to the attachment member 8 once the head 32 passes through the housing aperture 24.

The second surface 31 of the base 28 is provided with a double-sided adhesive tape, glue or some other known conventional fastener 36 which facilitates secure attachment of the attachment member 8 to an exterior surface 38 of a desired helmet 40. Such attachment usually occurs adjacent an exterior surface of the helmet 40 which accommodates the ears of a user. The helmet 40 is provided with a conventional strap 41 for securing the helmet 40 to the head of the user.

Each clip member 4 is provided with a pair of projecting prongs 42 which have an outwardly facing chamfer 44 thereon. A retaining lip 46 is provided adjacent a free, unattached end of each of the projecting prongs 42 to facilitate retainment of the clip member 4 within the cavity 20 of the clip housing 6. A central section of the clip member 4 is provided with an elongate slot 45 which allows the clip member 4 to be fully received within the clip housing 6 without experiencing any interference from the mushroom protrusion element 26 of the attachment member 8. The clip member 4 and the clip housing 6 are designed to have very sleek and aerodynamic contours so that they do not generate any substantial wind resistance during use.

As the clip member 4 is received or inserted into the cavity 20 of the clip housing 6, the pair of projecting prongs 42 of the clip member 4 are initially biased or squeezed inwardly toward one another by the opposed, inwardly facing surfaces of the clip housing 6. The chamfers 44 of the projecting prongs 42 facilitate biasing of the prongs 42 inwardly toward one another as the prongs 42 enter the cavity 20. Each opposed, inwardly facing surface of the clip housing 6 may be provided with a similar mating chamfer.

Once the clip member 4 is sufficiently received within the cavity 20 of the clip housing 6, each one of the retaining lips 46 of the prongs 42 engages with one of the pair of opposed openings 18 in the side wall of the clip housing 6 and such engagement allows re-expansion of the prongs 42 substantially back to the prongs' original positions. Such re-expansion causes the clip member 4 to be captively retained within the cavity 20 of the clip housing 6 due to the engagement between the retaining lips 46 and a mating housing retaining surface 47 of the clip housing 6. In order to release the clip member 4 from the cavity 20 of the clip housing 6, the user simply pinches or squeezes the prongs 42 inwardly toward one another, via the pair of opposed openings 18 provided in the clip housing 6, so that the two retaining lips 46 of the clip member 4 are clear of the mating housing retaining surface 47 and the clip member 4 can thereafter be fully retracted from the clip housing 6. Such engagement/disengagement feature is similar to that of conventional mating male and female clip members which are currently known in this art.

An opposite end portion of the clip member 4 is provided with at least one cross member 50, preferably another cross member 52 is also provided. A first end of the strap 10 is passed around the at least one cross member 50 to assist with securing the strap 10 to the clip member 4. The first end of the strap 10, which is passed around the cross member 50, is then attached to a central cross piece 54 of a conventional length adjustment member 12 by either sewing or otherwise fastening 56 the strap 10 thereto in a conventional manner. The second, opposite end of the strap 10 passes through the length adjustment member 12, in a conventional manner, and is attached to the coupling member 14 by either sewing or otherwise fastening 58 the second end of the strap thereto in a conventional manner. The length adjustment member 12 facilitates adjustment of the distance between the coupling member 14 and the clip member 4 to facilitate proper adjustment of desired protective eyewear 60, e.g. goggles, glasses, sun glasses, a wind screen, etc., relative to the helmet 40 during use. As such adjustment features are well known to those skilled in this art, a further detailed description concerning the same is not provided herein.

Figure 4:
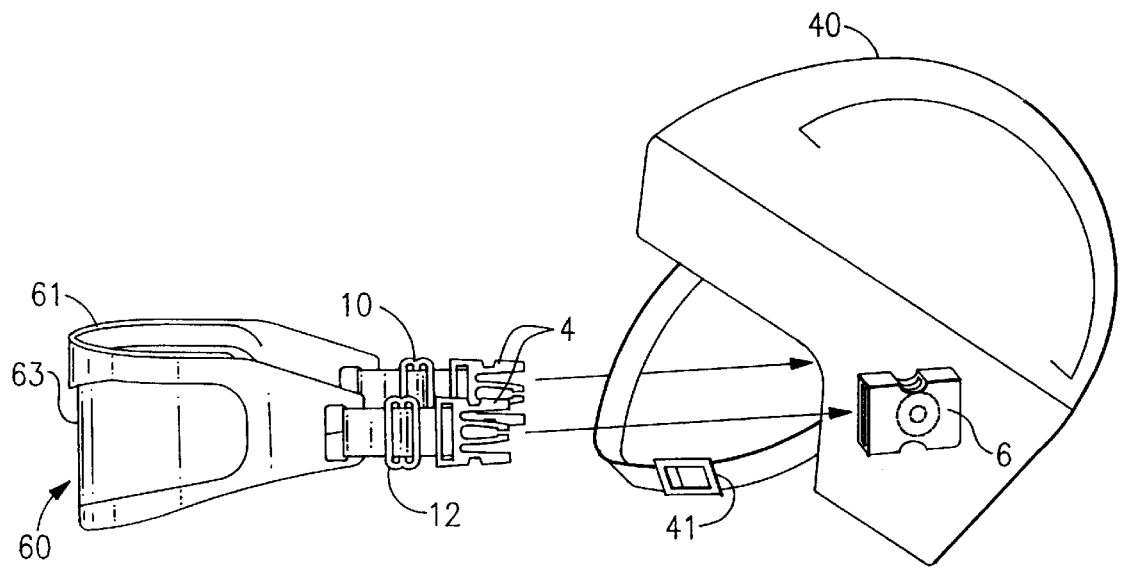
FIG. 4 shows a pair of strap members, secured to a pair of goggles, aligned for attachment to a helmet in accordance with the teaching of the present invention.
Figure 5:
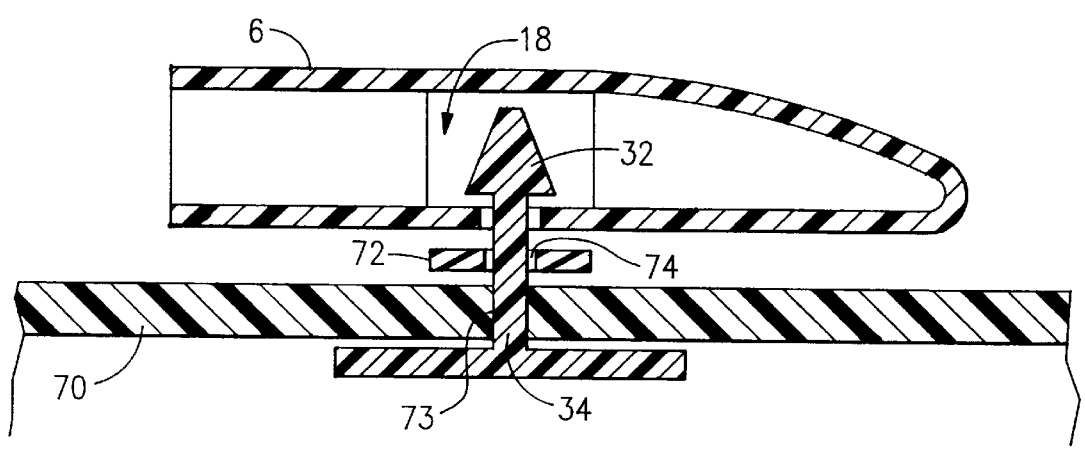
FIG. 5 is a diagrammatic cross-sectional view, of a second embodiment of the invention, showing the helmet, the attachment member, a retaining washer and the clip housing.

The protective eyewear 60 comprises a protective eyewear framework or housing 61 which supports a transparent lens 63 (FIG. 4). A first end portion of the protective eyewear housing 60 has a first end of the first strap 10 attached thereto, either by the coupling member 14 or directly by the first strap 10 in a conventional manner, e.g. passing the strap through an aperture and securing. A second opposite end of the first strap 10 has a first clip member 4 attached thereto. A second opposite end of the protective eyewear housing 61 has a first end of a second strap 10 attached thereto, either by the coupling member 14 or directly by the first strap 10 in a conventional manner, e.g. passing the strap through an aperture and securing. A second opposite end of the second strap 10 has a second clip member 4 attached thereto.

In order to employ the present invention, a user first secures the second surface 31 of each of the two bases 28 to the exterior surface of the helmet 40, one adjacent each area of the helmet 40 which accommodates the ears of a user. The exact placement or location is not critical as long as they are readily accessible. Once the two attachment members 8 are sufficiently secured thereto, a clip housing 6 is attached to each of the secured attachment members 8 by passing one of the heads 32 of the mushroom protrusion element 26 through a respective housing aperture 24 of the clip housing 6. Once the heads 32 are received by the clip housings 6, the clip housings 6 are retained by the secured attachment members 8 and allowed to pivot relative to the helmet 40. Thereafter, the clip member 4, the strap 10, the adjustment member 12 and the coupling member 14 are assembled with one another, as described above and shown in FIG. 2, to form the strap member 2. Next, a first one of the strap members 2 is attached to a first side of the protective eyewear housing 61, via the first coupling member 14, and a second one of the strap members 2 is attached to the opposite side of the pair of protective eyewear housing 61, via the second coupling member 14. When use of the protective eyewear 60 is desired, the user merely places the helmet 40 on his/her head and then engages the first one engages the first one of the clip members 4 with a first one of the clip housings 6 and then engages a second clip member 4 with a second one of the clip housings 6. Once this has occurred, the protective eyewear 60 is properly located for use. If necessary, the length of either or both strap members 2 can be readily altered by adjustment of the adjustment member 12.

To partially remove the protective eyewear 60, a first one of the clip members 4 is removed from the associated clip housing 6 by pitching or squeezing the two prongs 42 toward one another so that the associated clip member 4 can be easily and readily removed from the clip housing 6. If complete removal of the protective eyewear 60 is desired, the second one of the clip members 4 is removed from the second clip housings 6 in a similar manner.

A second embodiment of the invention, for attachment to a soft or flexible helmet 70, e.g. a leather bicycling helmet, is very similar to the first embodiment. The only difference between this embodiment and the first embodiment, is that a retaining washer 72 is provided for retaining the engagement between the attachment member 8 and the helmet 70. The soft helmet 70 is first provided with a helmet aperture 73, if one is not already provided therein. The mushroom protrusion element 26 of the attachment member 8 is then passed through the helmet aperture 73, provided in the soft helmet 70, and the retaining washer 72 is provided over the exposed mushroom protrusion element 26 to maintain engagement between the attachment member 8 and the helmet 70. The retaining washer 72 has an aperture 74 which is slightly smaller in diameter than the head 32 but sightly larger than the stem 34. This configuration allows the head 32 to pass through the aperture, while facilitating retention of the head 32 and rotation of the clip housing 6. A double-sided adhesive tape, glue or some other known conventional fastener, on the second surface of the base 28, is not necessary to facilitate secure attachment of the attachment member 8 to a desired helmet 70. In all other respects, this embodiment is the same as the previous embodiment of the present invention.

Figure 6:
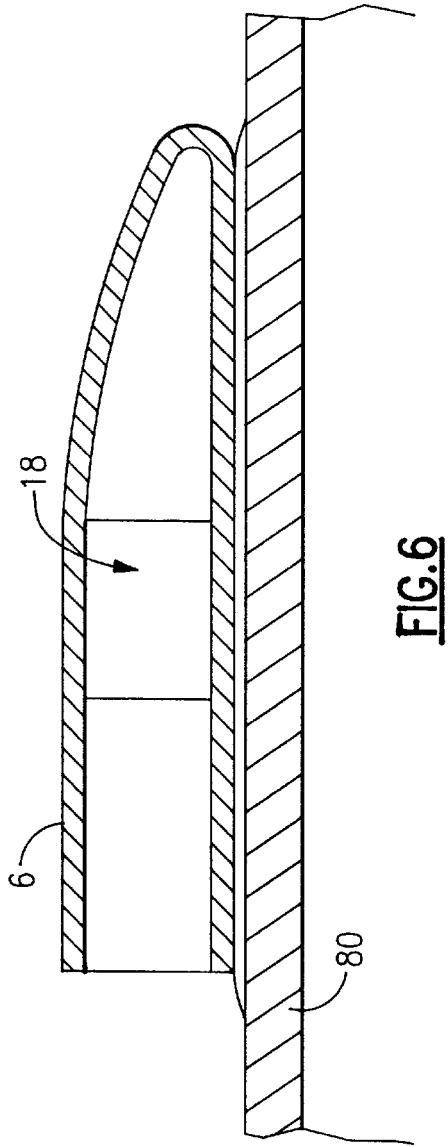
FIG. 6 is a diagrammatic cross-sectional view, of a third embodiment of the invention, showing permanent securement of the clip housing to the helmet.

It is to be appreciated that the clip housing 6 can also be molded with, or permanently secured directly to, the helmet (FIG. 6), e.g. on either an inwardly facing or an outwardly facing surface of the helmet, without affecting the integrity or the safety of the helmet 80. In such instance, the clip housing may not be a separate element and thus will not be able to pivot relative to the helmet 80—which pivoting motion is allowed in the two previous embodiments. In all other respects, this embodiment is the same as the previous two embodiments of the present invention.

Figure 7:
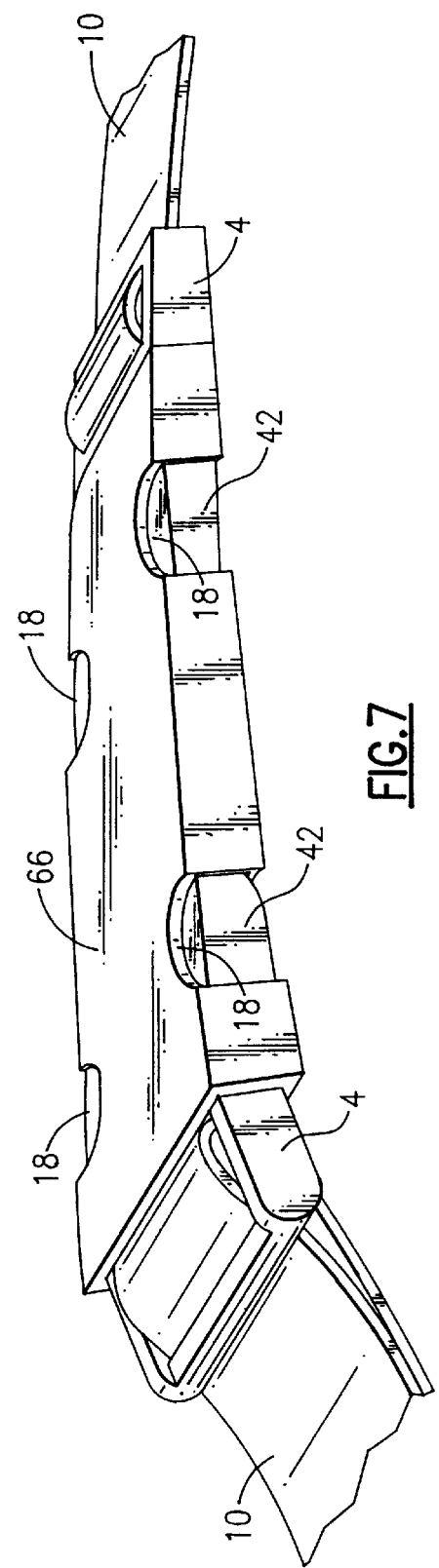
FIG. 7 is a diagrammatic cross-sectional view showing the engagement between a pair of clip members and a double clip housing.

If desired, a double clip housing 66, having a pair of opposed female clip housings 6 joined together end to end in an abutting relationship can be provided (FIG. 7). The double clip housing 66 is useful in receiving the two clip members 4, carried by an embodiment of protective eyewear 60, to convert the two separate strap members 2 into a continuous strap to facilitate wearing of the protective eyewear 60 in a conventional manner or carrying of the protective eyewear 60 on the arm of a user, for example. Such arrangement will minimize the possibility of losing or misplacing the protective eyewear 60.

Since certain changes may be made in the above described, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Wherefore, I/we claim:

1. A strapping system for coupling a protective eyewear housing to a helmet, said strapping system comprising:
    a first clip housing having a hollow interior cavity being sized to receive therein a first clip member, and said first clip member being repeatedly releasably engageable with said first clip housing;
    a second clip housing having a hollow interior cavity being sized to receive therein a second clip member, and said second clip member being repeatedly releasably engageable with said second clip housing;
    a first elongate strap having opposed first and second ends, the first end of said first elongate strap being securable to a first exterior portion of a protective eyewear housing and the second end of said first elongate strap being securable to said first clip member;
    a second elongate strap having opposed first and second ends, and the first end of said second elongate strap being securable to a second exterior portion of a protective eyewear housing and the second end of said second elongate strap being securable to said second clip member; and
    a first attachment member for securing said first clip housing to a helmet and a second attachment member for securing said second clip housing to a helmet;
    wherein each of said first and said second attachment members comprises a base which has a mushroom-shaped protrusion element extending perpendicularly from a first surface thereof, for attachment to one of said first and said second clip housings, and a second surface of said base is provided with an adhesive for securing said attachment member to a helmet.

2. The strapping system according to claim 1, wherein an intermediate section of each of said first and said second elongate straps supports an adjustment member to facilitate length adjustment of said first and said second elongate straps.

3. The strapping system according to claim 1, wherein the first end of both said first and said second elongate straps has a coupling member for securing the first ends of said first and said second elongate straps to respective first and second exterior portions of a protective eyewear housing.

4. The strapping system according to claim 1, wherein each of said first and said second clip housings has an exterior surface which is provided with a pair of opposed openings in a side wall thereof to facilitate release of one of said first and said second clip members, and said hollow cavity is sized to intimately receive a major portion of a leading end of one of said first and said second clip members.

5. The strapping system according to claim 1, wherein a bottom surface of each of said first and said second clip housings is provided with a housing aperture therein to facilitate receiving and locking engagement with said mushroom-shaped protrusion element of one of said first and said second attachment members, and each of said first and said second clip housings further has two opposed openings provided in a side wall thereof.

6. The strapping system according to claim 5, wherein each of said mushroom-shaped protrusion elements has a head which is larger in diameter than said housing aperture provided in one of said first and said second clip housings, and said head has a taper, at a remote end thereof, to facilitate passage of said head through said housing aperture and, once said head passes completely through said housing aperture, said head facilitates retention of one of said first and said second clip housings with said attachment member.

7. The strapping system according to claim 6, wherein a stem connects said head with said base, and said stem is slightly smaller in size than said housing aperture to facilitate rotation of said clip housing relative to said attachment member once said head passes through said housing aperture.

8. The strapping system according to claim 5, wherein each of said first and said second clip members is provided with a pair of projecting prongs which have an outwardly facing chamfer thereon, and a retaining lip is provided adjacent a free, unattached end of each of the projecting prongs to facilitate retainment of said first and said second clip members, within the interior cavity of said respective first and said second clip housings, via engagement of each said retaining lip with one of said two opposed openings provided in said side wall of said first and said second clip housings.

9. The strapping system according to claim 1, wherein a central section of each of said first and said second clip members is provided with an elongate slot which allows said first and said second clip members to be fully received within said respective first and said second clip housings without interference from said mushroom-shaped protrusion element of said attachment member.

10. The strapping system according to claim 1, wherein an end portion of each of said first and said second clip members, remote from said leading end, is provided with at least one cross member, the second end of said first elongate strap is passed around the at least one cross member of said first clip member to secure said first elongate strap thereto and the second end of said second elongate strap is passed around the at least one cross member of said second clip member to secure said second elongate strap thereto.

11. The strapping system according to claim 1 in combination with protective eyewear, wherein said protective eyewear comprises a protective eyewear housing which supports a transparent lens.

12. A strapping system in combination with a protective eyewear housing, supporting a lens, and a helmet, said system comprising:

a first end of said protective eyewear housing having a first end of an elongate strap attached thereto, and a second opposite end of said first strap having a first clip member attached thereto; and a second opposed end of said protective eyewear housing having a first end of a second strap attached thereto, and a second opposite end of said second strap having a second clip member attached thereto;

a first clip housing having a hollow interior cavity being sized to receive therein said first clip member, and said first clip member being repeatedly releasably engageable with said first clip housing;

a second clip housing having a hollow interior cavity being sized to receive therein said second clip member, and said second clip member being repeatedly releasably engageable with said second clip housing;

the first clip housing being secured to the helmet via a first attachment member and said second clip housing being secured to the helmet via a second attachment member;

wherein each said attachment member comprises a base having a mushroom-shaped protrusion element extending perpendicularly from a first surface thereof and a second surface of said base is provided with an adhesive for securing said attachment member to the helmet.

13. The combination according to claim 12, wherein both said first and said second clip housings each have a housing aperture formed therein, and once said mushroom-shaped protrusion element of one of said first and said second attachment members passes through said housing aperture, said first clip member is attached to said first attachment member and said second clip member is attached to said second attachment member to facilitate attachment of said first and said second clip members to the helmet.

14. The combination according to claim 12, wherein said mushroom-shaped protrusion element has a head which is larger in diameter than said housing aperture to facilitate retention of said first and said second clip housings by said respective first and said second attachment members.

15. The combination according to claim 14, wherein said head has a taper, at a remote free end thereof, to facilitate passage of said head through said housing aperture.

16. The combination according to claim 14, wherein a stem connects said head with said base, and said stem is slightly smaller in size than said housing aperture to facilitate rotation of said clip housing relative to said attachment member once said head passes through said housing aperture.

17. The combination according to claim 12, wherein a first retaining washer is provided for retaining engagement between said first attachment member and the helmet and a second retaining washer is provided for retaining engagement between said second attachment member and the helmet.

18. A method of utilizing a strapping system for coupling a protective eyewear housing and supporting a lens to a helmet, said method comprising the steps of:

forming a first clip housing with a hollow interior cavity being sized to receive therein a first clip member, and said first clip member being repeatedly releasably engageable with said first clip housing;

forming a second clip housing with a hollow interior cavity being sized to receive therein a second clip member, and said second clip member being repeatedly releasably engageable with said second clip housing;

providing first and said second elongate straps with opposed first and second ends;

securing the first end of said first elongate strap to a first exterior portion of said protective eyewear housing and securing the second end of said first elongate strap to said first clip member, and securing the first end of said second elongate strap to a second exterior portion of said protective eyewear housing and securing the second end of said second elongate strap to said second clip member;

securing said first clip housing to a helmet via a first attachment member and securing said second clip housing to the helmet via a second attachment member; and forming each of said first and said second attachment members with a base having a mushroom-shaped protrusion element extending perpendicularly from a first surface of said base and providing a second opposed surface of said base with an adhesive for securing said attachment member to the helmet.

19. The method according to claim 18, further comprising the steps of supporting a first adjustment member along an intermediate section of said first elongate strap to facilitate length adjustment of said first elongate strap and supporting a second adjustment member along an intermediate section of said second elongate strap to facilitate length adjustment of said second elongate strap.

20. The method according to claim 18, further comprising the steps of forming a pair of opposed openings in a side wall of said first clip housing, and sizing said hollow cavity of said first clip housing so as to intimately receive a major portion of a leading end of said first clip member; and forming a pair of opposed openings in a side wall of said second clip housing, and sizing said hollow cavity of said second clip housing so as to intimately receive a major portion of a leading end of said second clip member.

* * * * *